United States Patent
Li (10) Patent No.: US 11,564,581 B2
(45) Date of Patent: Jan. 31, 2023

(54) METHODS FOR ASSESSING FRACTIONAL FLOW RESERVE

(71) Applicant: BOSTON SCIENTIFIC SCIMED, INC., Maple Grove, MN (US)

(72) Inventor: Wenguang Li, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 364 days.

(21) Appl. No.: 16/047,763

(22) Filed: Jul. 27, 2018

(65) Prior Publication Data
US 2019/0038144 A1 Feb. 7, 2019

Related U.S. Application Data

(60) Provisional application No. 62/541,069, filed on Aug. 3, 2017.

(51) Int. Cl.
*A61B 5/026* (2006.01)
*A61B 5/00* (2006.01)
(Continued)

(52) U.S. Cl.
CPC .......... *A61B 5/026* (2013.01); *A61B 5/02158* (2013.01); *A61B 5/6851* (2013.01); *A61B 5/6852* (2013.01); *A61B 5/02007* (2013.01)

(58) Field of Classification Search
CPC .............. A61B 5/02007; A61B 5/0215; A61B 2562/0247; A61B 5/6851; A61B 5/6852;
(Continued)

(56) References Cited

U.S. PATENT DOCUMENTS 3,273,447 A 9/1966 Wallace
3,963,323 A 6/1976 Arnold
(Continued)

FOREIGN PATENT DOCUMENTS

CN 102469943 A 5/2012
DE 202014100938 U1 3/2014
(Continued)

OTHER PUBLICATIONS

International Search report and Written Opinion dated May 29, 2017 for International Application No. PCT/US2017/018905.
(Continued)

*Primary Examiner* — Christian Jang
*Assistant Examiner* — Karen E Toth
(74) *Attorney, Agent, or Firm* — Seager, Tufte & Wickhem LLP (57) ABSTRACT

Systems for determining fractional flow reserve are disclosed. An example system may include a pressure sensing guidewire for measuring a first pressure, a second pressure sensing medical device for measuring a second pressure, and a processor coupled to the pressure sensing guidewire and coupled to the second pressure sensing medical device. The processor may be designed to generate a plot of the magnitude of the second pressure over time, identify one or more time intervals of the plot that have a slope less than zero, determine a mean of the second pressure, and calculate the ratio of the first pressure to the second pressure when (a) the second pressure is less than or equal to the mean of the second pressure and (b) during the one or more time intervals when the slope of the plot is less than zero.

17 Claims, 3 Drawing Sheets

(51) Int. Cl.
*A61B 5/0215* (2006.01)
*A61B 5/02* (2006.01)

(58) Field of Classification Search
CPC ..... A61B 5/021; A61B 5/6876; A61B 5/7235;
A61B 5/7246; A61B 5/7275
See application file for complete search history.

(56) References Cited

U.S. PATENT DOCUMENTS

| | | | |
|---|---|---|---|
| 4,112,941 A | 9/1978 | Larimore |
| 4,771,782 A | 9/1988 | Millar |
| 4,893,630 A | 1/1990 | Roberts, Jr. |
| 4,953,553 A | 9/1990 | Tremulis |
| 5,106,455 A | 4/1992 | Jacobsen et al. |
| 5,135,503 A | 8/1992 | Abrams |
| 5,178,159 A | 1/1993 | Christian |
| 5,238,004 A | 8/1993 | Sahatjian et al. |
| 5,280,786 A | 1/1994 | Wlodarczyk |
| 5,313,957 A | 5/1994 | Little |
| 5,322,064 A | 6/1994 | Lundquist |
| 5,414,507 A | 5/1995 | Herman |
| 5,421,195 A | 6/1995 | Wlodarczyk |
| 5,422,969 A | 6/1995 | Eno |
| 5,425,371 A | 6/1995 | Mischenko |
| 5,427,114 A | 6/1995 | Colliver et al. |
| 5,437,288 A | 8/1995 | Schwartz |
| 5,438,873 A | 8/1995 | Wlodarczyk et al. |
| 5,450,853 A | 9/1995 | Hastings |
| 5,573,520 A | 11/1996 | Schwartz et al. |
| 5,633,963 A | 5/1997 | Rickenbach et al. |
| 5,748,819 A | 5/1998 | Szentesi et al. |
| 5,755,668 A | 5/1998 | Itoigawa et al. |
| 5,772,609 A | 6/1998 | Nguyen et al. |
| 5,779,698 A | 7/1998 | Clayman |
| 5,797,856 A | 8/1998 | Frisbie et al. |
| 5,836,885 A | 11/1998 | Schwager |
| 5,865,801 A | 2/1999 | Houser |
| 5,872,879 A | 2/1999 | Hamm |
| 5,873,835 A | 2/1999 | Hastings et al. |
| 5,902,248 A | 5/1999 | Millar et al. |
| 5,916,177 A | 6/1999 | Schwager |
| 5,938,624 A | 8/1999 | Akerfeldt et al. |
| 5,949,929 A | 9/1999 | Hamm |
| 5,964,714 A | 10/1999 | Lafontaine |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,461,301 B2 | 10/2002 | Smith |
| 6,508,803 B1 | 1/2003 | Horikawa et al. |
| 6,565,514 B2 | 5/2003 | Svanerudh et al. |
| 6,575,911 B2 | 6/2003 | Schwager |
| 6,579,246 B2 | 6/2003 | Jacobsen et al. |
| 6,579,484 B1 | 6/2003 | Tiernan et al. |
| 6,585,660 B2 | 7/2003 | Dorando et al. |
| 6,589,164 B1 | 7/2003 | Flaherty |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B1 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,491,484 B2 | 7/2013 | Lewis |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,585,613 B2 | 11/2013 | Nagano |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,757,893 B1 | 6/2014 | Isenhour et al. |
| 8,764,683 B2 | 7/2014 | Meller et al. |
| 8,920,870 B2 | 12/2014 | Weber |
| 8,936,401 B2 | 1/2015 | Belleville et al. |
| 8,998,823 B2 | 4/2015 | Manstrom et al. |
| 9,052,466 B2 | 6/2015 | Belleville et al. |
| 9,110,255 B2 | 8/2015 | Lin et al. |
| 9,149,230 B2 | 10/2015 | Caron |
| 9,289,137 B2 | 3/2016 | Corl |
| 2002/0013527 A1 | 1/2002 | Hoek |
| 2003/0031422 A1 | 2/2003 | Inagaki et al. |
| 2003/0069522 A1 | 4/2003 | Jacobsen et al. |
| 2003/0120175 A1 | 6/2003 | Ehr |
| 2003/0159518 A1 | 8/2003 | Sawatari |
| 2004/0073141 A1 | 4/2004 | Hartley et al. |
| 2004/0181174 A2 | 9/2004 | Davis et al. |
| 2004/0258370 A1 | 12/2004 | Bush |
| 2005/0000294 A1 | 1/2005 | Tenerz et al. |
| 2005/0141817 A1 | 6/2005 | Yazaki et al. |
| 2006/0074318 A1 | 4/2006 | Ahmed et al. |
| 2006/0122537 A1 | 6/2006 | Reynolds et al. |
| 2007/0010726 A1 | 1/2007 | Loeb |
| 2007/0055162 A1 | 3/2007 | Vlahos |
| 2008/0119758 A1 | 5/2008 | Samuelsson et al. |
| 2008/0285909 A1 | 11/2008 | Younge et al. |
| 2009/0082678 A1 | 3/2009 | Smith |
| 2009/0088650 A1 | 4/2009 | Corl |
| 2009/0116020 A1 | 5/2009 | Wu et al. |
| 2009/0192412 A1 | 7/2009 | Sela et al. |
| 2010/0022950 A1 | 1/2010 | Anderson et al. |
| 2010/0087605 A1 | 4/2010 | Yamamoto et al. |
| 2010/0145308 A1 | 6/2010 | Layman et al. |
| 2010/0234698 A1 | 9/2010 | Manstrom et al. |

(56) References Cited

U.S. PATENT DOCUMENTS

| | | |
|---|---|---|
| 2010/0241008 A1 | 9/2010 | Belleville et al. |
| 2011/0046477 A1 | 2/2011 | Hulvershorn et al. |
| 2011/0071407 A1 | 3/2011 | Hübinette et al. |
| 2011/0098572 A1 | 4/2011 | Chen et al. |
| 2011/0152721 A1 | 6/2011 | Sela |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0245808 A1 | 10/2011 | Voeller et al. |
| 2011/0319773 A1 | 12/2011 | Kanz et al. |
| 2012/0083794 A1 | 4/2012 | Martin et al. |
| 2012/0122051 A1 | 5/2012 | Hackel et al. |
| 2012/0210797 A1 | 8/2012 | Yu et al. |
| 2012/0227505 A1 | 9/2012 | Belleville et al. |
| 2012/0238869 A1 | 9/2012 | Schmitt et al. |
| 2012/0245457 A1 | 9/2012 | Crowley |
| 2012/0259273 A1 | 10/2012 | Moshinsky et al. |
| 2012/0265102 A1 | 10/2012 | Leo et al. |
| 2013/0046190 A1 | 2/2013 | Davies |
| 2013/0051731 A1 | 2/2013 | Belleville et al. |
| 2013/0190633 A1 | 7/2013 | Dorando |
| 2013/0218032 A1 | 8/2013 | Belleville |
| 2013/0296718 A1 | 11/2013 | Ranganathan et al. |
| 2013/0296722 A1 | 11/2013 | Warnking et al. |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0066789 A1 | 3/2014 | Nishigishi et al. |
| 2014/0081244 A1 | 3/2014 | Voeller et al. |
| 2014/0103273 A1 | 4/2014 | Nakajima |
| 2014/0107624 A1 | 4/2014 | Belleville |
| 2014/0121475 A1 | 5/2014 | Alpert et al. |
| 2014/0135633 A1* | 5/2014 | Anderson ............. A61B 5/026 600/486 |
| 2014/0180028 A1 | 6/2014 | Burkett |
| 2014/0205235 A1 | 7/2014 | Benjamin et al. |
| 2014/0241669 A1 | 8/2014 | Belleville et al. |
| 2014/0248021 A1 | 9/2014 | Belleville et al. |
| 2014/0276109 A1 | 9/2014 | Gregorich |
| 2014/0309533 A1 | 10/2014 | Yamashika |
| 2014/0350414 A1 | 11/2014 | McGowan et al. |
| 2015/0003783 A1 | 1/2015 | Benjamin et al. |
| 2015/0003789 A1 | 1/2015 | Webler |
| 2015/0051499 A1 | 2/2015 | McGowan |
| 2015/0078714 A1 | 3/2015 | Isenhour et al. |
| 2015/0112210 A1 | 4/2015 | Webler |
| 2015/0133800 A1 | 5/2015 | McCaffrey |
| 2015/0141842 A1 | 5/2015 | Spanier |
| 2015/0198774 A1 | 7/2015 | Lin et al. |
| 2015/0230713 A1* | 8/2015 | Merritt ................. A61B 5/7278 600/486 |
| 2015/0230714 A1 | 8/2015 | Davies et al. |
| 2015/0301288 A1 | 10/2015 | Thornton, Jr. |
| 2015/0305633 A1 | 10/2015 | McCaffrey |
| 2015/0323747 A1 | 11/2015 | Leigh et al. |

FOREIGN PATENT DOCUMENTS

| | | |
|---|---|---|
| EP | 0235992 A1 | 9/1987 |
| EP | 0738495 A1 | 10/1996 |
| EP | 0879615 A1 | 11/1998 |
| EP | 0879617 A1 | 11/1998 |
| EP | 1039321 A2 | 9/2000 |
| EP | 0750879 B1 | 11/2000 |
| EP | 1136032 A1 | 9/2001 |
| EP | 1136036 A1 | 9/2001 |
| EP | 1136036 B1 | 2/2003 |
| EP | 1136032 B1 | 9/2003 |
| EP | 1479407 A1 | 11/2004 |
| EP | 1925958 A1 | 5/2008 |
| EP | 1927316 A1 | 6/2008 |
| GB | 1440761 A | 6/1976 |
| GB | 2300978 A | 11/1996 |
| JP | 53-141644 A | 12/1978 |
| JP | 08-257128 A | 10/1996 |
| JP | 08-280634 A | 10/1996 |
| JP | 10-501339 A1 | 2/1998 |
| JP | 10-337280 A | 12/1998 |
| JP | 11-258476 A | 9/1999 |
| JP | 2005-291945 A | 10/2005 |
| JP | 2008-304731 A | 12/2008 |
| JP | 2009-10182 A | 1/2009 |
| JP | 2010-233883 A | 10/2010 |
| JP | 2013-132886 A | 7/2013 |
| JP | 2014-42645 A | 3/2014 |
| WO | 9313707 A1 | 7/1993 |
| WO | 9533983 A1 | 12/1995 |
| WO | 9626671 A1 | 9/1996 |
| WO | 9945352 A1 | 9/1999 |
| WO | 2007/058616 A1 | 5/2007 |
| WO | 2007/130163 A1 | 11/2007 |
| WO | 2008/034010 A2 | 3/2008 |
| WO | 2008/076931 A2 | 6/2008 |
| WO | 2009/042865 A1 | 4/2009 |
| WO | 2011/027282 A1 | 3/2011 |
| WO | 2011/090744 A2 | 7/2011 |
| WO | 2011/123689 A1 | 10/2011 |
| WO | 2012/000798 A1 | 1/2012 |
| WO | 2012/090210 A1 | 7/2012 |
| WO | 2012/091783 A1 | 7/2012 |
| WO | 2013/033489 A1 | 3/2013 |
| WO | 2014/025255 A1 | 2/2014 |
| WO | 2015/059311 A1 | 4/2015 |
| WO | 2017013020 A1 | 1/2017 |

OTHER PUBLICATIONS

International Search Report and Written Opinion dated Oct. 22, 2018 for International Application No. PCT/US2018/044153.

Van't Veer et al., "Comparison of Different Diastolic Resting Indexes to iFR. Are They Equal?", Journal of American College of Cardiology, 70(25): 3088-3096, Dec. 18, 2017.

Abe et al., "Diastolic Fractional Flow Reserve to Assess the Functional Severity of Moderate Coronary Artery Stenoses: Comparison with Fractional Flow Reserve and Coronary Flow Velocity Reserve", Circulation, pp. 2365-2370, Nov. 7, 2000.

Hennigan et al., "Discordance Between Resting and Hyperemic Indices of Coronary Stenosis Severity: The VERIFY 2 Study (A Comparative Study of Resting Coronary Pressure Gradient, Instantaneous Wave-Free Ratio and Fractional Flow Reserve in an Unselected Population Referred for Invasive Angiography)", Circ. Cardiovascular Interventions, pp. 1-9, 2016.

Jeremias et al., "Multicenter Core Laboratory Comparison of the Instantaneous Wave-Free Ratio and Resting Pd/Pa with Fractional Flow Reserve: The RESOLVE Study", Journal of the American College of Cardiology Foundation, pp. 1253-1261, 2014.

* cited by examiner

METHODS FOR ASSESSING FRACTIONAL FLOW RESERVE

CROSS-REFERENCE TO RELATED APPLICATIONS

This application claims the benefit of priority under 35 U.S.C. § 119 to U.S. Provisional Application Ser. No. 62/541,069, filed Aug. 3, 2017, the entirety of which is incorporated herein by reference.

TECHNICAL FIELD

The present disclosure pertains to medical devices, and methods for using medical devices. More particularly, the present disclosure pertains to methods for assessing fractional flow reserve.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing methods, and use alternatives for medical devices. An example medical device includes a system for determining fractional flow reserve. The system comprises: a pressure sensing guidewire for measuring a first pressure; a second pressure sensing medical device for measuring a second pressure; a processor coupled to the pressure sensing guidewire and coupled to the second pressure sensing medical device; wherein the processor is designed to: generate a plot of the magnitude of the second pressure over time, identify one or more time intervals of the plot that have a slope less than zero, determine a mean of the second pressure, and calculate the ratio of the first pressure to the second pressure when (a) the second pressure is less than or equal to the mean of the second pressure and (b) during the one or more time intervals when the slope of the plot is less than zero.

Alternatively or additionally to any of the embodiments above, the pressure sensing guidewire includes an optical pressure sensor.

Alternatively or additionally to any of the embodiments above, the pressure sensing guidewire includes a tubular member having a proximal region with a first inner diameter and a distal region with a second inner diameter different from the first inner diameter.

Alternatively or additionally to any of the embodiments above, the second pressure sensing medical device includes a catheter with a pressure sensor.

Alternatively or additionally to any of the embodiments above, the first pressure, the second pressure, or both are wirelessly transmitted to the processor.

Alternatively or additionally to any of the embodiments above, the pressure sensing guidewire is designed to be disposed distal of an intravascular lesion.

Alternatively or additionally to any of the embodiments above, the second pressure sensing medical device is designed to be disposed proximal of an intravascular lesion.

Alternatively or additionally to any of the embodiments above, the processor is designed to calculate the ratio of the first pressure to the second pressure in the absence of a hyperemic agent.

Alternatively or additionally to any of the embodiments above, the processor is coupled to a display.

Alternatively or additionally to any of the embodiments above, the display is designed to display the plot.

A system for determining fractional flow reserve is disclosed. The system comprises: a pressure sensing guidewire for measuring a distal pressure at a location distal of a lesion; a pressure sensing catheter for measuring an aortic pressure; a processor coupled to the pressure sensing guidewire and coupled to the pressure sensing catheter; and wherein the processor is designed to: generate a plot of the magnitude of the aortic pressure over time, identify one or more time intervals of the plot that have a slope less than zero, determine a mean of the aortic pressure, and calculate the ratio of the distal pressure to the aortic pressure when (a) the aortic pressure is less than or equal to the mean of aortic pressure and (b) during the one or more time intervals when the slope of the plot is less than zero.

Alternatively or additionally to any of the embodiments above, the pressure sensing guidewire includes an optical pressure sensor.

Alternatively or additionally to any of the embodiments above, the pressure sensing guidewire includes a tubular member having a proximal region with a first inner diameter and a distal region with a second inner diameter different from the first inner diameter.

Alternatively or additionally to any of the embodiments above, the processor is designed to calculate the ratio of the distal pressure to the aortic pressure in the absence of a hyperemic agent.

Alternatively or additionally to any of the embodiments above, the processor is coupled to a display.

Alternatively or additionally to any of the embodiments above, the processor is designed to scale the mean aortic pressure by a scaling factor in the range of 0.75 to 1.25.

Alternatively or additionally to any of the embodiments above, the processor is designed to reject time intervals when the aortic pressure is less than a pressure lower bound.

A method for determining fractional flow reserve is disclosed. The method comprises: disposing a pressure sensing guidewire distal of an intravascular lesion; measuring a distal pressure with the pressure sensing guidewire; disposing a pressure sensing catheter in a vascular region; measuring an aortic pressure with the pressure sensing catheter; wherein a processor is coupled to the pressure sensing guidewire and coupled to the pressure sensing catheter; wherein the processor is designed to: generate a plot of the magnitude of the aortic pressure over time, identify one or more time intervals of the plot that have a slope less than zero, and determine a mean of the aortic pressure; and calculating a ratio of the distal pressure to the aortic pressure when (a) the aortic pressure is less than or equal to the mean of the aortic pressure (b) during the one or more time intervals when the slope of the plot is less than zero.

Alternatively or additionally to any of the embodiments above, measuring a distal pressure with the pressure sensing guidewire includes measuring the distal pressure in the absence of a hyperemic agent, wherein measuring an aortic pressure with the pressure sensing catheter includes measuring the aortic pressure in the absence of a hyperemic agent, or both.

Alternatively or additionally to any of the embodiments above, calculating a ratio of the distal pressure to the aortic pressure includes calculating the ratio of the distal pressure to the aortic pressure in the absence of a hyperemic agent.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as a ratio of the pressure after, or distal, of a stenosis (e.g., the distal pressure, $P_d$) relative to the pressure before the stenosis and/or the aortic pressure (e.g., the aortic pressure, $P_a$). In other words, FFR may be understood as $P_d/P_a$.

Figure 1:
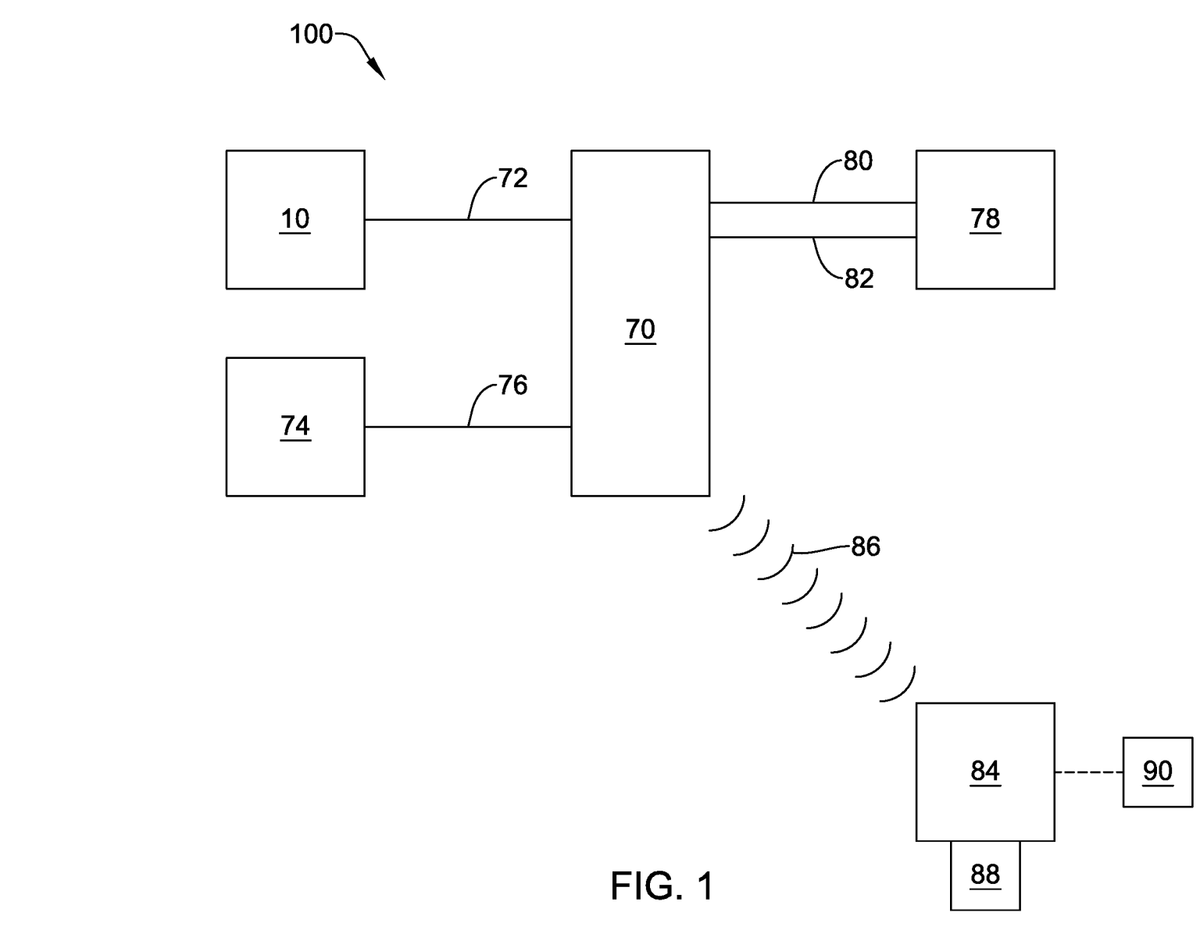
FIG. 1 schematically illustrates an example system for assessing fractional flow reserve.

An example system 100 for assessing/determining FFR is schematically represented in FIG. 1. The system 100 may include a first pressure sensing medical device 10. In at least some instances, the first pressure sensing medical device 10 may take the form of a pressure sensing guidewire 10. Some additional detail regarding the form of the guidewire 10, provided as an example, is disclosed herein. In other instances, the first pressure sensing medical device 10 may be a catheter or other type of pressure sensing medical device. The pressure sensing guidewire 10 may be utilized to measure blood pressure distal of an intravascular stenosis, e.g., the distal pressure $P_d$. The first pressure sensing medical device 10 may be coupled to a linking device 70. In some instances, this may include directly attaching the first pressure sensing medical device 10 to the linking device 70. In other instances, another structure such as a connector cable (not shown) may be used to couple the first pressure sensing medical device 10 to the linking device 70. When the first pressure sensing medical device 10 is coupled to the linking device 70, a first pressure data 72 may be communicated between the first pressure sensing medical device 10 and the linking device 70. It is noted that in FIG. 1, a line is drawn between the first pressure sensing medical device 10 and the linking device 70 to represent the coupling of the first pressure sensing medical device 10 and the linking device 70. In addition the line between the first pressure sensing medical device 10 and the linking device 70 is labeled with reference number 72 in order to represent the transmission of the first pressure data 72 (and/or the first pressure data 72 itself). In at least some instances, the first pressure data 72 is the distal pressure $P_d$.

The system 100 may also include a second pressure sensing medical device 74. In at least some instances, the second pressure sensing medical device 74 may take the form of a pressure sensing catheter. However, other devices are contemplated including pressure sensing guidewires or other devices. The second pressure sensing medical device 74 may be utilized to measure blood pressure proximal of an intravascular stenosis and/or the aortic pressure, e.g., the aortic pressure $P_a$. The second pressure sensing medical device 74 may also be coupled to the linking device 70 and may communicate a second pressure data 76 between the second pressure sensing medical device 74 and the linking device 70. It is noted that in FIG. 1, a line is drawn between the second pressure sensing medical device 74 and the linking device 70 to represent the coupling of the second pressure sensing medical device 74 and the linking device 70. In addition the line between the second pressure sensing medical device 74 and the linking device 70 is labeled with reference number 76 in order to represent the transmission of the second pressure data 76 (and/or the second pressure data 76 itself). In at least some instances, the second pressure data 76 is the aortic pressure $P_a$.

In some instances, the linking device 70 may communicate with a hemodynamic system 78 (e.g., a hemodynamic display system 78). When doing so, data representative of the distal pressure $P_d$ (represented by reference number 80) may be communicated to the hemodynamic system 78 and data representative of the aortic pressure $P_a$ (represented by reference number 82) may be communicated to the hemodynamic system 78. In some instances, both connections between the linking device 70 and the hemodynamic system 78 (e.g., for communicating $P_d$ and $P_a$) may be wired connections. In other instances, one or both of the connections may be wireless connections. In still other instances, both $P_d$ and $P_a$ may be communicated along a single wired connection.

In some instances, the linking device 70 may also communicate with a processing and/or display system 84. When doing so, data representative of the distal pressure $P_d$ and data representative of the aortic pressure $P_a$ (both the distal pressure $P_d$ and the aortic pressure $P_a$ data are represented by reference number 86 in FIG. 1) may be communicated to the processing and/or display system 84. In at least some instances, $P_d$ and $P_a$ may be communicated between the linking device 70 and the processing and/or display system 84 using a wireless connection. In other instances, one or both of $P_d$ and $P_a$ may be communicated between the linking device 70 and the processing and/or display system 84 with a wired connection.

The processing and/or display system 84 may include a processor 88. The processor 88 may be an integrated component of the processing and/or display system 84 (e.g., the processor 88 may be disposed within the same housing as the processing and/or display system 84) or the processor 88 may be separate component of the processing and/or display system 84 and coupled therewith. The processor 88 may be coupled to the first pressure sensing medical device 10 and coupled to the second pressure sensing medical device 74 such that pressure measurements (e.g., $P_d$ and $P_a$) may be received by the processor 88 from the first pressure sensing medical device 10 and the second pressure sensing medical device 74. The processor 88 may be designed to and/or otherwise be capable of performing a number of calculations, executing instructions, etc. For example, the processor may be designed to calculate/determine the mean distal pressure $P_d$ (e.g., as measured by the first pressure sensing medical device 10 over one or more cardiac cycles), calculate/determine the mean aortic pressure $P_a$ (e.g., as measured by the second pressure sensing medical device 74 over one or more cardiac cycles), plot the distal pressure $P_d$ and/or the aortic pressure $P_a$ over time, calculate/determine the slope of the plot of the distal pressure $P_d$ and/or the slope of the plot of the aortic pressure $P_a$ (e.g., at various points along the plot), or the like. A display 90 may be coupled to or otherwise integrated with the processing and/or display system 84. The display 90 may display various data received from first pressure sensing medical device 10 and the second pressure sensing medical device 74, plots of the pressure data as generated by the processor 80, etc.

When determining FFR, it may be desirable to measure a change or drop in pressure across a stenosis while under a maximum flow condition (e.g., hyperemia). Thus, a number of interventions that are performed to assess FFR include the administration of hyperemic agents such as adenosine to cause maximum flow conditions. For a number of reasons (e.g., patient comfort, extended procedure time, technical challenges associated with mixing adenosine for intravascular administration, cost, etc.), it may be desirable to reduce the use of hyperemic agents. Pressure measurements performed under a resting condition conduction are typically referred as resting indices. An example of such a measurement is resting $P_d/P_a$ in which the ratio is computed with data from the whole cardiac cycle. Disclosed herein are methods for assessing/determining FFR that can be performed in the absence of hyperemic agents including adenosine.

The maximum coronary flow occurs during the diastolic period of the cardiac cycle. Therefore, measurements of $P_d$ and $P_a$ during a diastolic period may provide a ratio closer to FFR (e.g., a better approximation of FFR) than that obtained from the whole cardiac cycle. In addition to resting $P_d/P_a$, some methods for assessing FFR may include computing $P_d$ and $P_a$ during time windows from the diastolic period. For example, some interventions such as instantaneous wave-free ratio and/or iFR™ may attempt to measure FFR during diastole. Such methods may require accurate measurement of waveform timing and/or synchronization with an ECG, which may complicate the process for assessing/determining FFR. Disclosed herein are methods for assessing/determining FFR by monitoring $P_d$ and $P_a$ during specific windows during the diastolic period of the cardiac cycle. The methods for assessing/determining FFR disclosed herein are relatively straightforward to implement such that FFR can be assessed/determined in a timely manner that enhances the comfort for the patient and that does not require unnecessary additional processes and/or synchronization.

Figure 2:
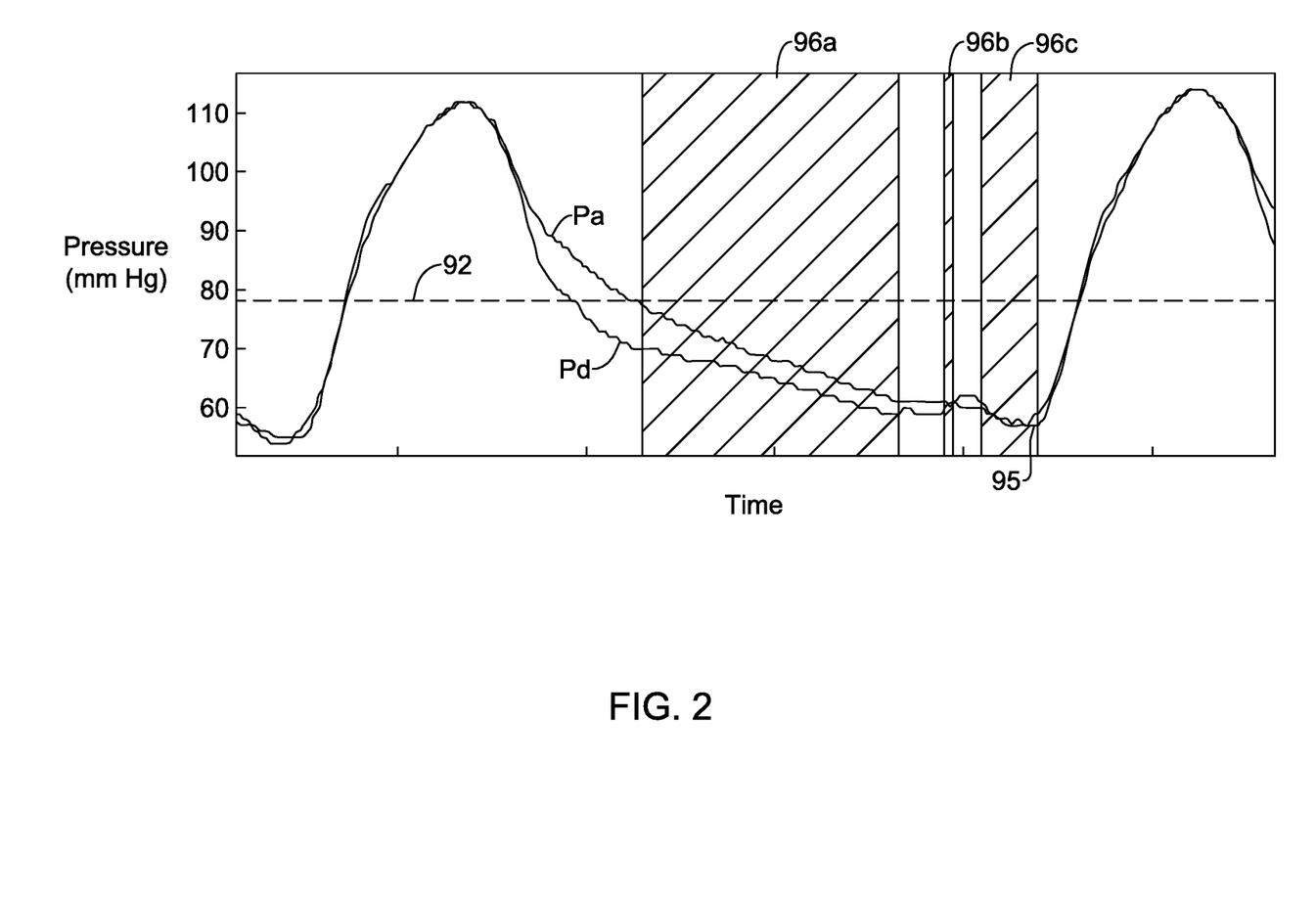
FIG. 2 graphically depicts blood pressure values over time.

FIG. 2 graphically depicts pressure measurements over a number of cardiac cycles (e.g., one full cycle is depicted plus a portion of another cardiac cycle). In this example, a graphical depiction of $P_d$ (e.g., as measured by the first pressure sensing medical device 10) and a graphical depiction of $P_a$ (e.g., as measured by the second pressure sensing medical device 74) are shown over time. Also shown is the mean aortic pressure 92.

In order to assess/determine FFR, the processor 88 may be utilized to perform a number of tasks including:

generating a plot of the magnitude of the distal pressure $P_d$ (e.g., as measured by the first pressure sensing medical device 10 and as depicted in FIG. 2) over time, generating a plot of the magnitude of the aortic pressure $P_a$ (e.g., as measured by the second pressure sensing medical device 74 and as depicted in FIG. 2) over time, identifying one or more time intervals of the plot of $P_a$ where the slope of the plot is less than zero, calculating/determining the mean aortic pressure 92, one or more additional calculations, and/or combinations thereof.

In one example, regions of the cardiac cycle are identified where:

(a) $P_a$ is less than or equal to the mean aortic pressure 92, and (b) the slope $P_a$ is less than zero.

In another example, regions of the cardiac cycle are identified where:

(a) $P_a$ is less than or equal to the mean aortic pressure 92 scaled by a scaling factor ranging from 0.5 to 1.5, or about 0.75 to 1.25, or about 0.95 to 1.05 (e.g., regions of the cardiac cycle are identified where $P_a$ is less than or equal to the mean aortic pressure 92 multiplied by the scaling factor), and (b) the slope $P_a$ is less than zero.

In another example, regions of the cardiac cycle are identified where:

(a) $P_a$ is less than or equal to the mean aortic pressure 92 is scaled by a scaling factor ranging from 0.5 to 1.5, or about 0.75 to 1.25, or about 0.95 to 1.05, and/or (b) the slope $P_a$ is less than zero, and/or (c) $P_a$ is higher than a pressure lower bound, which can be determined by one of the following methods:
  i) a fixed negative offset with a range of −10 mmHg-−100 mmHg from the mean aortic pressure 92,
  ii) a relative negative offset from the mean aortic pressure 92 as computed by 10%-100% of the mean aortic pressure 92, and/or
  iii) a fixed positive offset with a range of 10 mmHg-100 mmHg from the minimum aortic pressure 95.

The mean aortic pressure 92 may be determined for each individual cardiac cycle or across a number of cardiac cycles. Time windows or regions that meet these criteria are believed to be during high flow periods (e.g., during the diastolic period) and are believed to be suitable for use in assessing/determining FFR. Thus, the system 100 can be utilized to assess/determine/calculate FFR during these periods in the absence of hyperemic agents and/or without the need for unnecessary additional processes and/or synchronization. In the graph shown in FIG. 2, three time regions 96a, 96b, 96c are defined that meet these criteria. It can be appreciated that in other plots/graphs, fewer or more time regions may be identified. The processor 88 can be utilized to assess/determine/calculate FFR during these time regions 96a, 96b, 96c.

Figure 3:
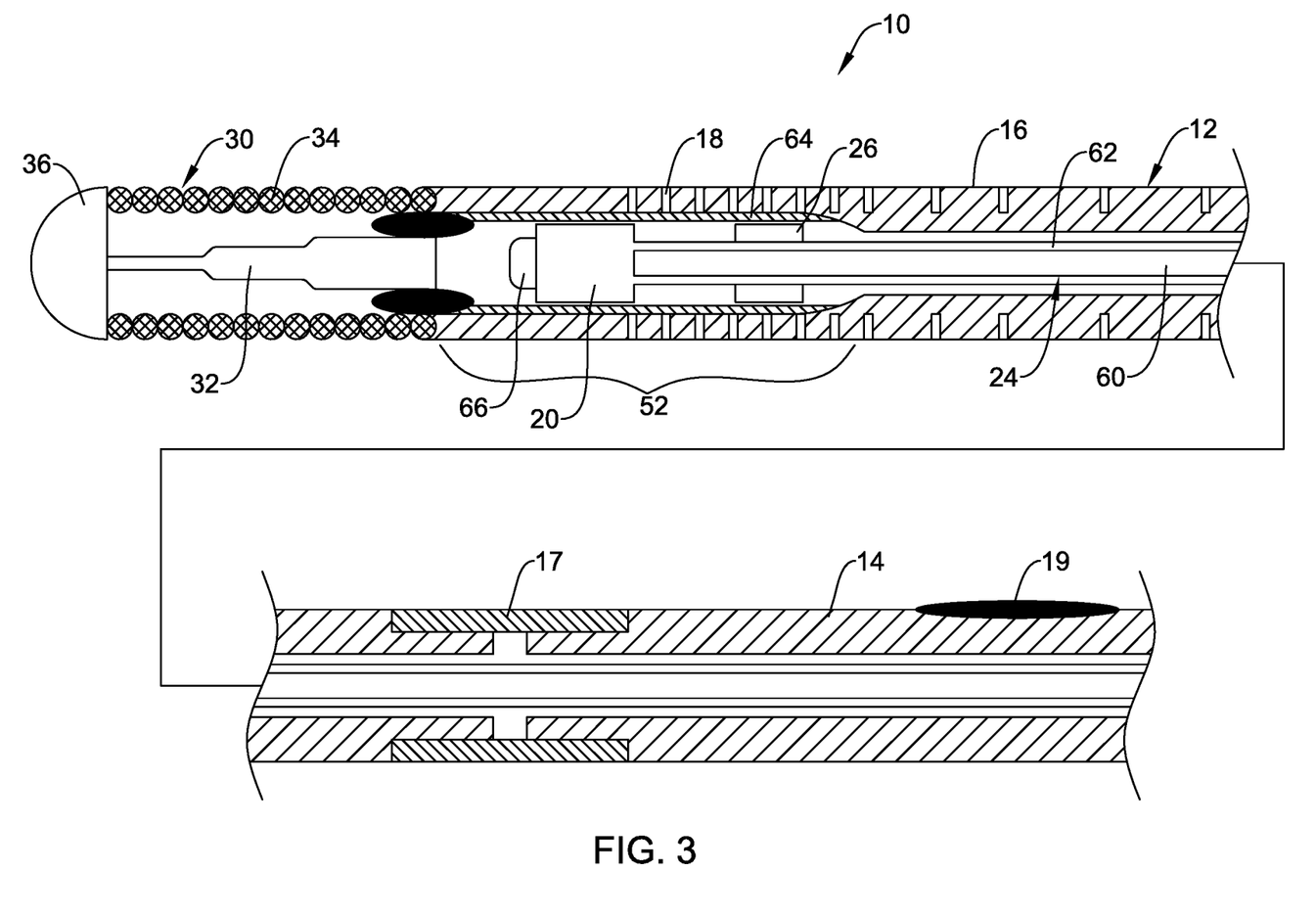
FIG. 3 is a partial cross-sectional side view of a portion of an example medical device.

FIG. 3 illustrates a portion of the first pressure sensing medical device 10 that may be part of the system 100. In this example, the first pressure sensing medical device 10 is a blood pressure sensing guidewire 10. However, this is not intended to be limiting as other medical devices are contemplated including, for example, catheters, shafts, leads, wires, or the like. The guidewire 10 may include a shaft or tubular member 12. The tubular member 12 may include a proximal region 14 and a distal region 16. The materials for the proximal region 14 and the distal region 16 may vary and may include those materials disclosed herein. For example, the distal region 16 may include a nickel-cobalt-chromium-molybdenum alloy (e.g., MP35-N). The proximal region 14 may be made from the same material as the distal region 16 or a different material such as stainless steel. These are just examples. Other materials are contemplated.

In some embodiments, the proximal region 14 and the distal region 16 are formed from the same monolith of material. In other words, the proximal region 14 and the distal region 16 are portions of the same tube defining the tubular member 12. In other embodiments, the proximal region 14 and the distal region 16 are separate tubular members that are joined together. For example, a section of the outer surface of the portions 14/16 may be removed and a sleeve 17 may be disposed over the removed sections to join the regions 14/16. Alternatively, the sleeve 17 may be simply disposed over the regions 14/16. Other bonds may also be used including welds, thermal bonds, adhesive bonds, or the like. If utilized, the sleeve 17 used to join the proximal region 14 with the distal region 16 may include a material that desirably bonds with both the proximal region 14 and the distal region 16. For example, the sleeve 17 may include a nickel-chromium-molybdenum alloy (e.g., INCONEL).

A plurality of slots 18 may be formed in the tubular member 12. In at least some embodiments, the slots 18 are formed in the distal region 16. In at least some embodiments, the proximal region 14 lacks slots 18. However, the proximal region 14 may include slots 18. The slots 18 may be desirable for a number of reasons. For example, the slots 18 may provide a desirable level of flexibility to the tubular member 12 (e.g., along the distal region 16) while also allowing suitable transmission of torque. The slots 18 may be arranged/distributed along the distal region 16 in a suitable manner. For example, the slots 18 may be arranged as opposing pairs of slots 18 that are distributed along the length of the distal region 16. In some embodiments, adjacent pairs of slots 18 may have a substantially constant spacing relative to one another. Alternatively, the spacing between adjacent pairs may vary. For example, more distal regions of the distal region 16 may have a decreased spacing (and/or increased slot density), which may provide increased flexibility. In other embodiments, more distal regions of the distal region 16 may have an increased spacing (and/or decreased slot density). These are just examples. Other arrangements are contemplated.

A pressure sensor 20 may be disposed within the tubular member 12 (e.g., within a lumen of tubular member 12). While the pressure sensor 20 is shown schematically in FIG. 3, it can be appreciated that the structural form and/or type of the pressure sensor 20 may vary. For example, the pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, the pressure sensor 20 may include an optical pressure sensor. In at least some of these embodiments, an optical fiber or fiber optic cable 24 (e.g., a multimode fiber optic) may be attached to the pressure sensor 20 and may extend proximally therefrom. The optical fiber 24 may include a central core 60 and an outer cladding 62. In some instances, a sealing member (not shown) may attach the optical fiber 24 to the tubular member 12. Such an attachment member may be circumferentially disposed about and attached to the optical fiber 24 and may be secured to the inner surface of the tubular member 12 (e.g., the distal region 16). In addition, a centering member 26 may also be bonded to the optical fiber 24. In at least some embodiments, the centering member 26 is proximally spaced from the pressure sensor 20. Other arrangements are contemplated. The centering member 26 may help reduce forces that may be exposed to the pressure sensor 20 during navigation of guidewire and/or during use.

In at least some embodiments, the distal region 16 may include a region with a thinned wall and/or an increased inner diameter that defines a sensor housing region 52. In general, the sensor housing region 52 is the region of distal region 16 that ultimately "houses" the pressure sensor 20. By virtue of having a portion of the inner wall of the tubular member 12 being removed at the sensor housing region 52, additional space may be created or otherwise defined that can accommodate the sensor 20. The sensor housing region 52 may include one or more openings such as one or more distal porthole openings 66 that provide fluid access to the pressure sensor 20.

A tip member 30 may be coupled to the distal region 16. The tip member 30 may include a core member 32 and a spring or coil member 34. A distal tip 36 may be attached to the core member 32 and/or the spring 34. In at least some embodiments, the distal tip 36 may take the form of a solder ball tip. The tip member 30 may be joined to the distal region 16 of the tubular member 12 with a bonding member 46 such as a weld.

The tubular member 12 may include an outer coating 19. In some embodiments, the coating 19 may extend along substantially the full length of the tubular member 12. In other embodiments, one or more discrete sections of the tubular member 12 may include the coating 19. The coating 19 may be a hydrophobic coating, a hydrophilic coating, or the like. The tubular member 12 may also include an inner coating 64 (e.g., a hydrophobic coating, a hydrophilic coating, or the like) disposed along an inner surface thereof. For example, the hydrophilic coating 64 may be disposed along the inner surface of the housing region 52. In some of these and in other instances, the core member 32 may include a coating (e.g., a hydrophilic coating). For example, a proximal end region and/or a proximal end of the core member 32 may include the coating. In some of these and in other instances, the pressure sensor 20 may also include a coating (e.g., a hydrophilic coating).

The materials that can be used for the various components of the system 100 and/or the guidewire 10 may include those commonly associated with medical devices. For simplicity purposes, the following discussion makes reference to the tubular member 12 and other components of the guidewire 10. However, this is not intended to limit the devices and methods described herein, as the discussion may be applied to other tubular members and/or components of tubular members or devices disclosed herein.

The tubular member 12 and/or other components of the guidewire 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of guidewire 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the guidewire 10 to achieve the same result.

In some embodiments, a degree of Magnetic Resonance Imaging (MRI) compatibility is imparted into the guidewire 10. For example, the guidewire 10, or portions thereof, may be made of a material that does not substantially distort the image and create substantial artifacts (e.g., gaps in the image). Certain ferromagnetic materials, for example, may not be suitable because they may create artifacts in an MRI image. The guidewire 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A system for determining fractional flow reserve in the absence of administering a hyperemic agent, the system comprising:
   a pressure sensing guidewire for measuring a first pressure;
   a second pressure sensing medical device for measuring a second pressure; and a processor coupled to the pressure sensing guidewire and coupled to the second pressure sensing medical device, the processor arranged to execute instructions, which instructions when executed cause the processor to:

receive an indication of the first pressure from the pressure sensing guidewire for a first time period during a medical intervention, receive an indication of the second pressure from the second pressure sensing medical device for the first time period, calculate a slope of a plot of the second pressure over the first time period, calculate a mean of the second pressure over the first time period, identify one or more regions of a cardiac cycle within the first time period where the second pressure is less than or equal to the mean of the second pressure and where the slope of the plot of the second pressure is less than or equal to zero, calculate a fractional flow reserve (FFR) as the ratio of the first pressure over the second pressure using only the identified one or more regions of the cardiac cycle, and display the FFR on a display coupled to the system during the medical intervention, wherein the medical intervention occurs in the absence of a hyperemic agent.

2. The system of claim 1, wherein the pressure sensing guidewire includes an optical pressure sensor.

3. The system of claim 1, wherein the pressure sensing guidewire includes a tubular member having a proximal region with a first inner diameter and a distal region with a second inner diameter different from the first inner diameter.

4. The system of claim 1, wherein the second pressure sensing medical device includes a catheter with a pressure sensor.

5. The system of claim 1, wherein the first pressure, the second pressure, or both are wirelessly transmitted to the processor.

6. The system of claim 1, wherein the pressure sensing guidewire is designed to be disposed distal of an intravascular lesion.

7. The system of claim 1, wherein the second pressure sensing medical device is designed to be disposed proximal of an intravascular lesion.

8. The system of claim 1, wherein the system comprises the display.

9. The system of claim 1, wherein the processor, when executing the instructions is further caused to output the plot to the display.

10. A system for determining fractional flow reserve, the system comprising:

a pressure sensing guidewire for measuring a distal pressure at a location distal of a lesion;

a pressure sensing catheter for measuring an aortic pressure; a processor coupled to the pressure sensing guidewire and coupled to the pressure sensing catheter, the processor arranged to execute instructions, which instructions when executed cause the processor to:

receive, during a medical intervention, an indication of the distal pressure from the pressure sensing guidewire for a first time period, receive, an indication of the aortic pressure from the pressure sensing catheter for the first time period, calculate a slope of a plot of the aortic pressure over the first time period, calculate a mean of the aortic pressure over the first time period, identify one or more regions of a cardiac cycle within the first time period where the aortic pressure is less than or equal to the mean of the aortic pressure and where the slope of the plot of the aortic pressure is less than or equal to zero, calculate a fractional flow reserve (FFR) as the ratio of the distal pressure over the aortic pressure using only the identified one or more regions of the cardiac cycle, and display, during the medical intervention, the FFR on a display coupled to the system, wherein the distal pressure and the aortic pressure are measured during the first time period in the absence of a hyperemic agent.

11. The system of claim 10, wherein the pressure sensing guidewire includes an optical pressure sensor.

12. The system of claim 10, wherein the pressure sensing guidewire includes a tubular member having a proximal region with a first inner diameter and a distal region with a second inner diameter different from the first inner diameter.

13. The system of claim 10, wherein the processor, when executing the instructions is further caused to output the plot to the display.

14. The system of claim 10, wherein the processor, when executing the instructions is further caused to:

scale the mean of the aortic pressure by multiplying the mean of the aortic pressure by a scaling factor in the range of 0.75 to 1.25, and identify the one or more regions of a cardiac cycle within the first time period where the aortic pressure is less than or equal to the mean of the aortic pressure multiplied by the scaling factor and where the slope of the plot of the aortic pressure is less than or equal to zero.

15. A method for determining fractional flow reserve, the method comprising:

receiving, at a processor from a pressure sensing guidewire disposed distal of an intravascular lesion during a medical intervention, a distal pressure-over a first time period;

receiving, at the processor from a pressure sensing catheter disposed in a vascular region during the medical intervention, an aortic pressures over the first time period;

calculating, by the processor, a slope of a plot of the aortic pressure over the first time period;

calculating, by the processor, a mean of the aortic pressure over the first time period;

identifying, by the processor, one or more regions of a cardiac cycle within the first time period where the aortic pressure is less than or equal to the mean of the aortic pressure and where the slope of the plot of the aortic pressure is less than or equal to zero;

calculating, by the processor, a fractional flow reserve (FFR) as the ratio of the distal pressure over the aortic pressure using only the identified one or more regions of the cardiac cycle; and displaying, on a display during the medical intervention, the FFR, wherein the distal pressure and the aortic pressure are measured in the absence of a hyperemic agent.

16. The method of claim 15, wherein measuring a distal pressure with the pressure sensing guidewire includes measuring the distal pressure in the absence of a hyperemic agent, wherein measuring an aortic pressure with the pressure sensing catheter includes measuring the aortic pressure in the absence of a hyperemic agent, or both.

17. The method of claim 15, wherein the processor is designed to output the plot to a display.

* * * * *